United States Patent [19]
Sherts

[11] Patent Number: 6,022,367
[45] Date of Patent: *Feb. 8, 2000

[54] SURGICAL APPARATUS FOR FORMING A HOLE IN A BLOOD VESSEL

[75] Inventor: Charles R. Sherts, Wesport, Conn.

[73] Assignee: United States Surgical, Norwalk, Conn.

[ * ] Notice: This patent issued on a continued prosecution application filed under 37 CFR 1.53(d), and is subject to the twenty year patent term provisions of 35 U.S.C. 154(a)(2).

[21] Appl. No.: 08/877,990

[22] Filed: Jun. 18, 1997

[51] Int. Cl.⁷ .................................................. A61B 17/32
[52] U.S. Cl. ........................................... 606/184; 606/185
[58] Field of Search ................................... 606/184, 185, 606/170; 30/119; 227/180.1

[56] References Cited

U.S. PATENT DOCUMENTS

| | | |
|---|---|---|
| D. 281,721 | 12/1985 | Scanlan . |
| D. 372,310 | 7/1996 | Hartnett . |
| 2,864,370 | 12/1958 | Alvos ........................................ 606/181 |
| 3,776,237 | 12/1973 | Hill et al. . |
| 4,018,228 | 4/1977 | Goosen ..................................... 606/184 |
| 4,122,855 | 10/1978 | Tezel . |
| 4,216,776 | 8/1980 | Downie et al. ........................... 606/184 |
| 4,243,048 | 1/1981 | Griffin . |
| 4,388,925 | 6/1983 | Burns . |
| 4,469,109 | 9/1984 | Mehl . |
| 4,699,154 | 10/1987 | Lindgren . |
| 4,733,671 | 3/1988 | Mehl . |
| 4,738,261 | 4/1988 | Enstrom . |
| 4,785,826 | 11/1988 | Ward . |
| 4,832,045 | 5/1989 | Goldberger . |
| 4,931,042 | 6/1990 | Holmes et al. ........................... 606/185 |
| 5,005,585 | 4/1991 | Mazza . |
| 5,129,913 | 7/1992 | Ruppert . |
| 5,139,508 | 8/1992 | Kantrowitz et al. . |
| 5,172,702 | 12/1992 | Leigh et al. . |
| 5,183,053 | 2/1993 | Yeh et al. . |
| 5,186,178 | 2/1993 | Yeh et al. . |
| 5,192,294 | 3/1993 | Blake ....................................... 606/184 |
| 5,304,193 | 4/1994 | Zhadanov . |
| 5,403,338 | 4/1995 | Milo ........................................ 606/184 |
| 5,423,330 | 6/1995 | Lee . |
| 5,515,861 | 5/1996 | Smith . |
| 5,688,286 | 11/1997 | Yoon ........................................ 606/185 |
| 5,702,412 | 12/1997 | Popov et al. ............................. 606/170 |

FOREIGN PATENT DOCUMENTS 2028070  12/1971  Germany ................................. 606/184

*Primary Examiner*—Michael H. Thaler

[57] ABSTRACT

The present application provides a surgical apparatus for forming a hole in a vessel comprising a housing, an elongated member extending from the housing, a penetrating tip having a cutting blade extending from the elongated member, and a hole cutter positioned proximally of the penetrating tip. The penetrating tip preferably includes a shield protecting the cutting blade, the shield being movable from a first position shielding the blade to a second position exposing the blade. The shield is preferably spring biased distally to the first position, is forced proximally by the vessel wall during penetration, and returns to the first position upon penetration through the wall. An actuator is moved from a first position to a second position to advance the annular cutter.

20 Claims, 9 Drawing Sheets

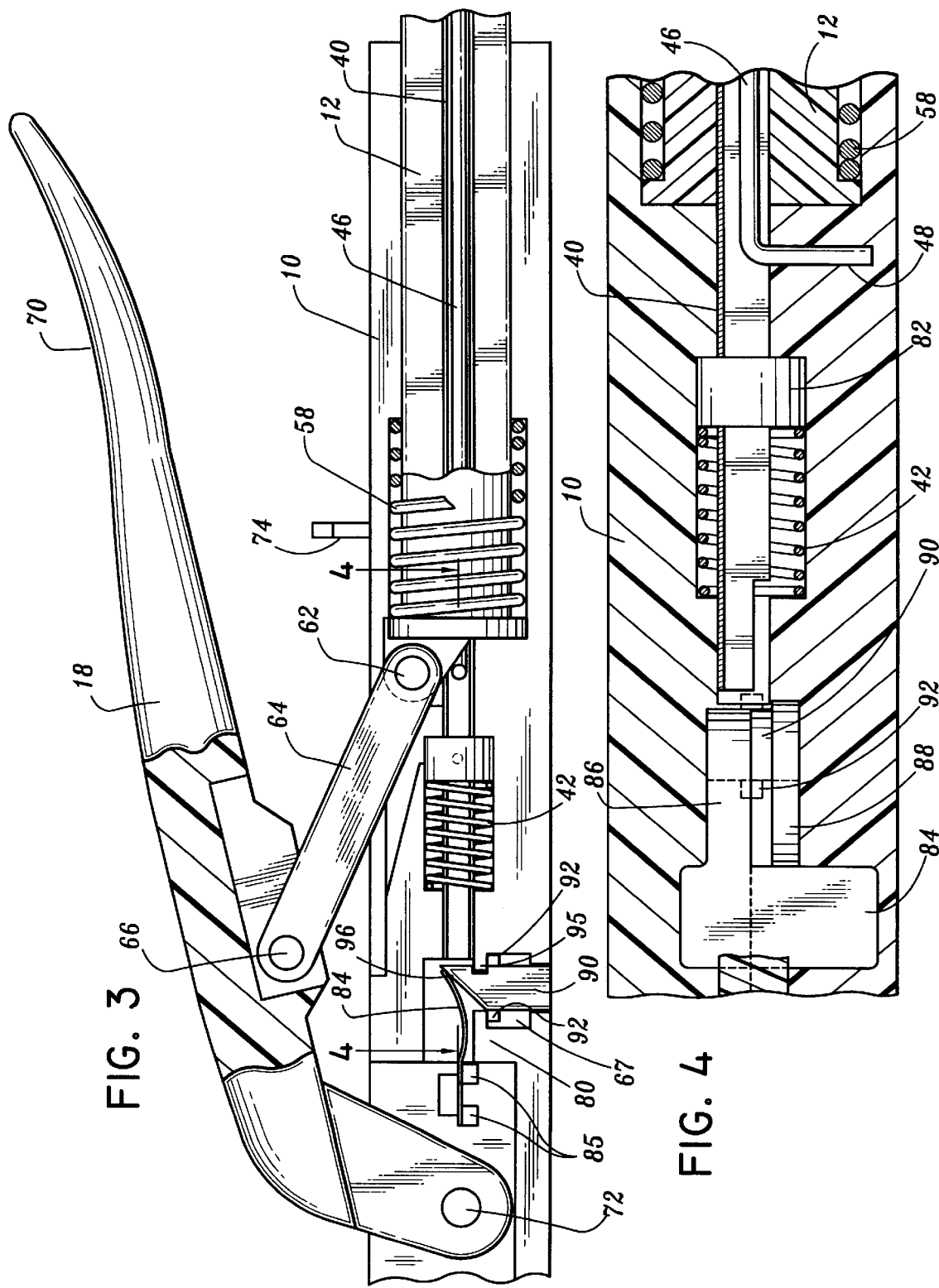

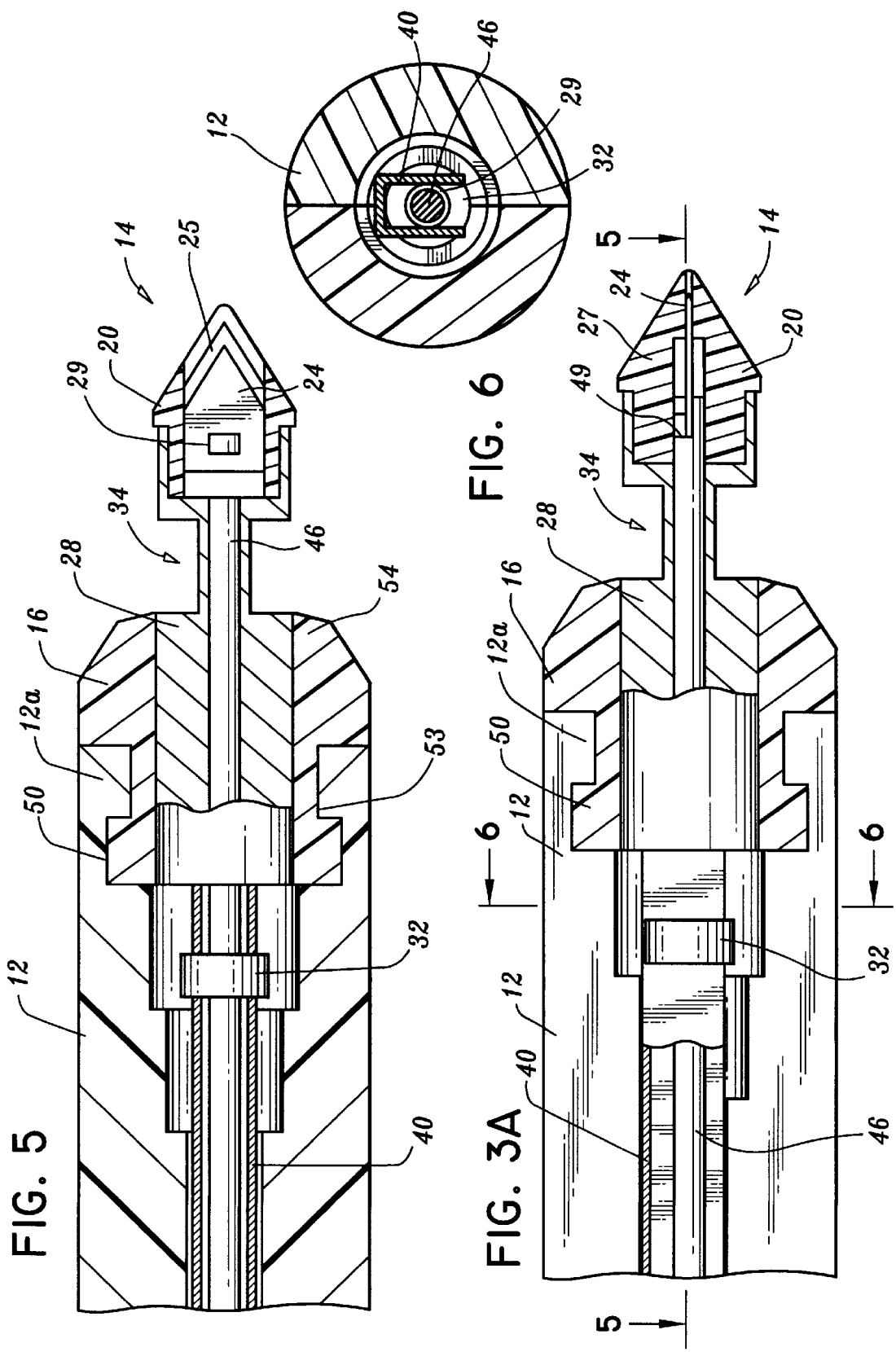

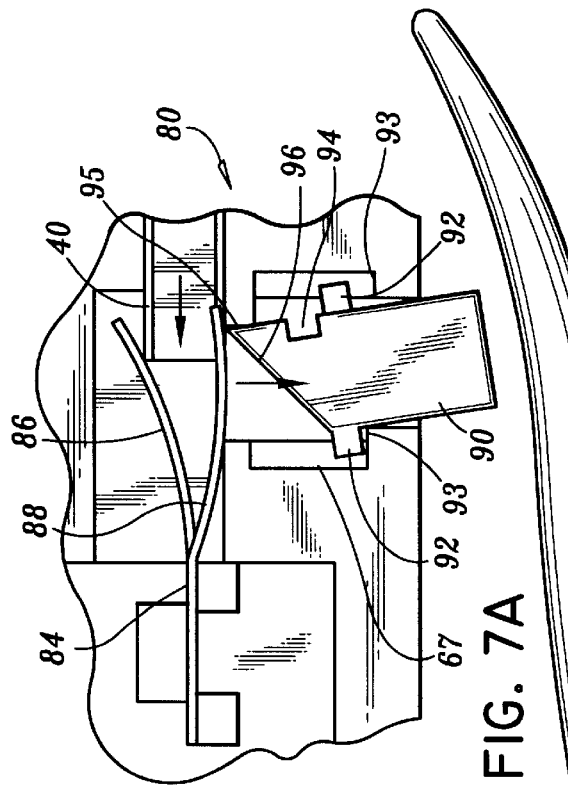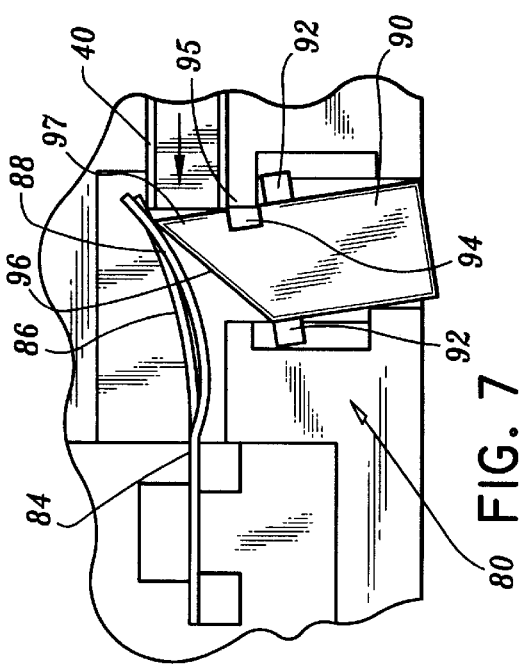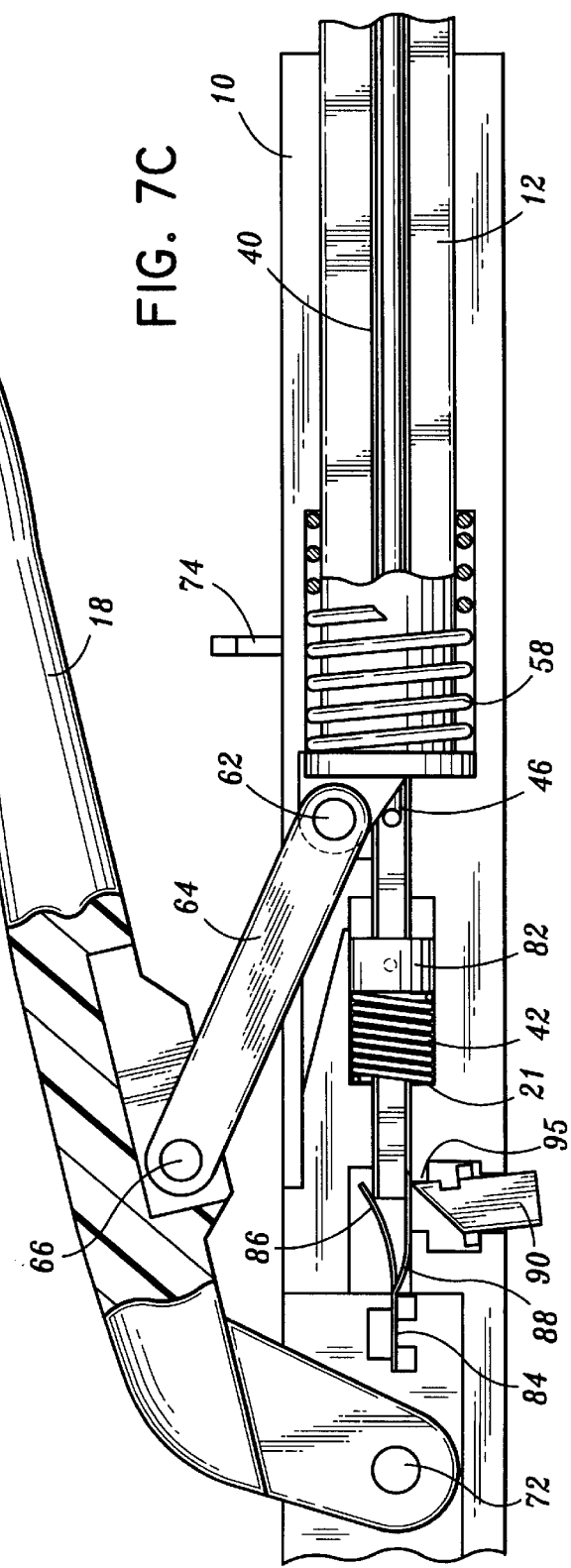

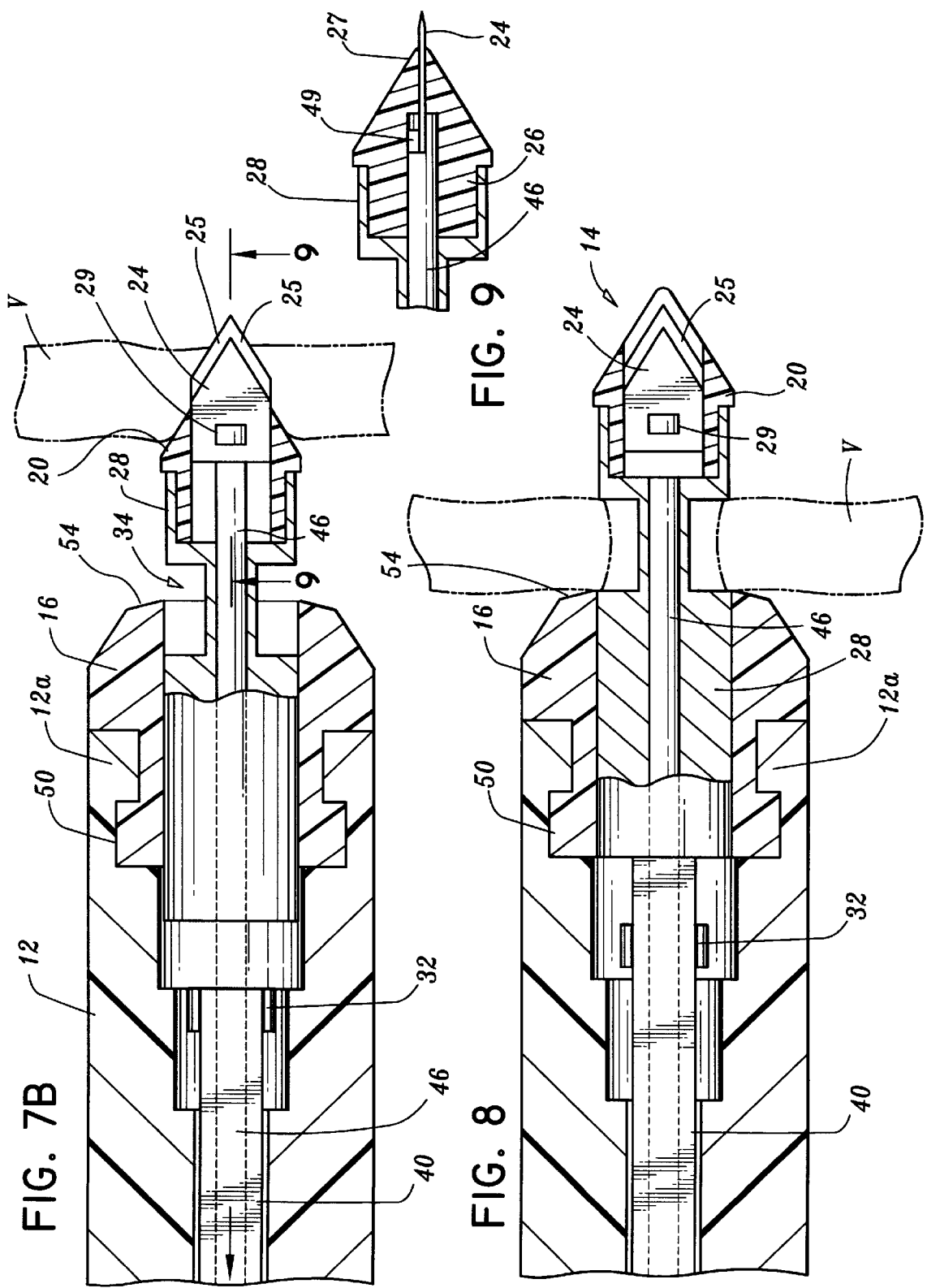

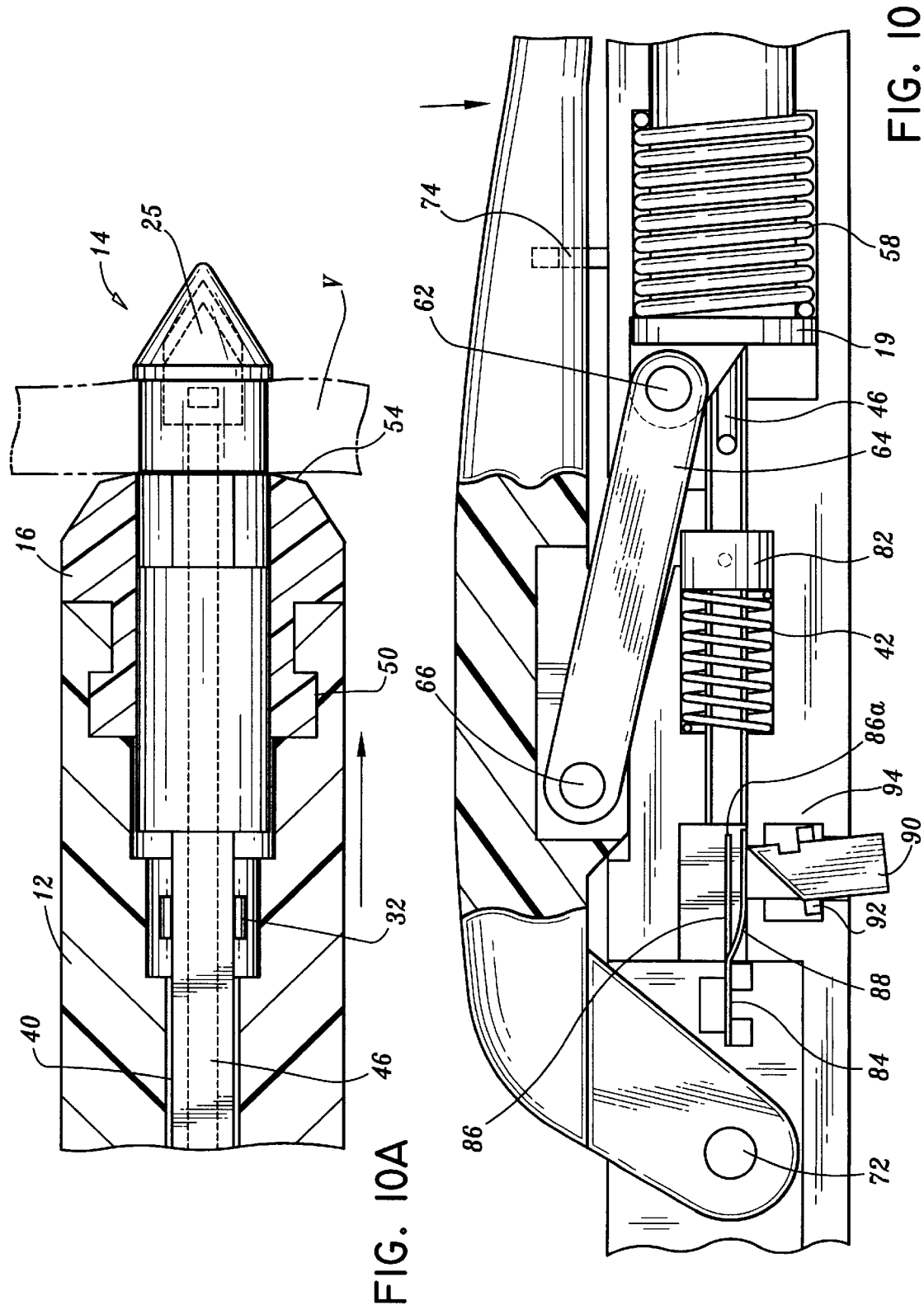

SURGICAL APPARATUS FOR FORMING A HOLE IN A BLOOD VESSEL

BACKGROUND

1. Technical Field

The application relates to a surgical apparatus and more particularly to a surgical apparatus for forming a hole in a vessel wall.

2. Background of Related Art

In heart bypass surgery, it is necessary to attach a graft to the patient's aorta to divert blood flow away from the constricted vessel so it instead flows from the aorta through the graft. Typically, a scalpel incision is made in the aorta and an instrument, commonly known as an aortic punch, is inserted into the incision to punch a circular hole. The graft can then be attached to the aorta at the site of the circular hole. Examples of aortic punch instruments are disclosed in U.S. Pat. No. 4,018,228 to Goosen and U.S. Pat. No. 4,216,776 to Downie. Since the aorta is a region of relatively high pressure blood flow, the initial scalpel incision causes a great deal of bleeding which can obstruct the site and inhibit insertion of the aortic punch. Also, by adversely affecting visibility, the time required to perform the surgical procedure is increased.

To reduce the amount of blood caused by the initial scalpel incision, some surgeons clamp the portion of the aorta adjacent the region where the scalpel incision is to be made. This reduces the blood flow when the surgeon makes the incision. However, since it is likely that there is plaque buildup on the inside wall of the aorta, clamping the aorta could detach the plaque from the wall, sending it into the patient's bloodstream which can cause a stroke or other harm to the patient.

The need therefore exists for an instrument and method to facilitate insertion of an aortic punch without requiring clamping the aorta.

SUMMARY

The present application provides a surgical apparatus for forming a hole in a vessel wall comprising a housing, an elongated member extending from the housing, a penetrating tip having a cutting blade extending from the elongated member, and a hole cutter positioned proximally of the penetrating tip. The penetrating tip preferably includes a shield protecting the cutting blade, the shield being movable from a first position shielding the blade to a second position exposing the blade. The shield is preferably spring biased distally to the first position, is forced proximally by the vessel wall during penetration, and returns to the first position upon penetration through the wall.

An actuator extends from the housing and is actuable to cause relative movement between the hole cutter and the penetrating tip to form a hole in the blood vessel. Preferably, the hole cutter is spring biased proximally and the actuator moves the hole cutter distally towards the shield to form a hole in the vessel wall.

A latch may be provided to retain the actuator in the actuated position to thereby maintain the hole cutter in a distal position to encapsulate the severed tissue within the cutter. A locking mechanism may also be provided to prevent subsequent retraction of the shield after it has been once retracted and advanced. Preferably, the locking mechanism includes a spring movable between a first position to allow retraction of the shield and a second position to prevent retraction of the shield. A reset button may be provided to move the spring from the second position to the first position to allow subsequent retraction of the shield.

The present application also provides a surgical apparatus for forming a hole in the vessel wall comprising a housing, an elongated member extending from the housing and including a cutter, a tissue receiving member positioned distal of the cutter, an actuator movable to an actuated position to cause relative movement of the cutter and the tissue receiving member, and a retaining mechanism retaining the actuator in the actuated position to retain the cut tissue between the cutter and tissue receiving member. The tissue receiving member is preferably a circumferential recessed portion formed on a rod member extending through an axial bore in the cutter.

A surgical apparatus for making a hole in a blood vessel wall is also provided comprising means for penetrating the blood vessel wall to provide entry of a tip of the instrument into the blood vessel, and means for forming a hole in the blood vessel wall wherein the forming means includes a cutter having an axial opening to receive the cut vessel wall portion. The penetrating means preferably includes a cutting blade and a distally biased blade shield movable during penetration of the vessel wall. A locking mechanism may be provided configured to prevent subsequent retraction of the shield after the shield has been once retracted and advanced.

A method of forming a hole in a blood vessel wall is also provided comprising the steps of inserting a penetrating tip of an apparatus directly through the wall to form an access incision for the apparatus and advancing a cutter relative to the penetrating tip to form a hole in the blood vessel wall. The method may further include the step of locking the penetrating tip in a retracted position to encapsulate the cut tissue.

BRIEF DESCRIPTION OF THE DRAWINGS

Various embodiments of the surgical apparatus of the subject application will be described below with reference to the following drawings wherein:

FIG. 3 is a side view in partial cross section of the apparatus showing the actuator in the unactuated position and the button, inner channel and outer tube in the initial position;

FIG. 3A is a cross-sectional view taken along lines 3A—3A of FIG. 1 showing the shield in the extended position to protect the cutting blade;

FIG. 4 is a cross sectional view taken along lines 4—4 of FIG. 3;

FIG. 5 is a cross-sectional view taken along lines 5—5 of FIG. 3A showing the shield in the extended position;

FIG. 6 is a cross sectional view taken along lines 6—6 of FIG. 3A;

FIG. 7 is an enlarged side view showing the button tabs released from the shelf as the shield (and inner channel) starts to retract;

FIG. 7A is a view similar to FIG. 7 showing the position of the button when the shield is fully retracted;

FIG. 7B is a view similar to FIG. 5 showing the shield in the retracted position to expose the cutting blade to penetrate tissue;

FIG. 7C is a side view in partial cross section showing the proximal end of the instrument when the actuator is in the unactuated position and the shield is in the fully retracted position;

FIG. 8 is a view similar to FIG. 7B showing the completion of tissue penetration and the shield returned to its extended (distal) position to shield the blade;

FIG. 9 is a cross-sectional view taken along lines 9—9 of FIG. 7B showing the shield in the retracted position to expose the blade;

FIG. 10 is a view similar to FIG. 7C showing the actuator in the actuated position to advance the annular cutter and the shield restrained by the spring locking mechanism;

FIG. 10A is a view similar to FIG. 5 showing the position of the annular cutter when the actuator is in the position of FIG. 10;

DETAILED DESCRIPTION OF THE PREFERRED EMBODIMENTS

Figure 1:
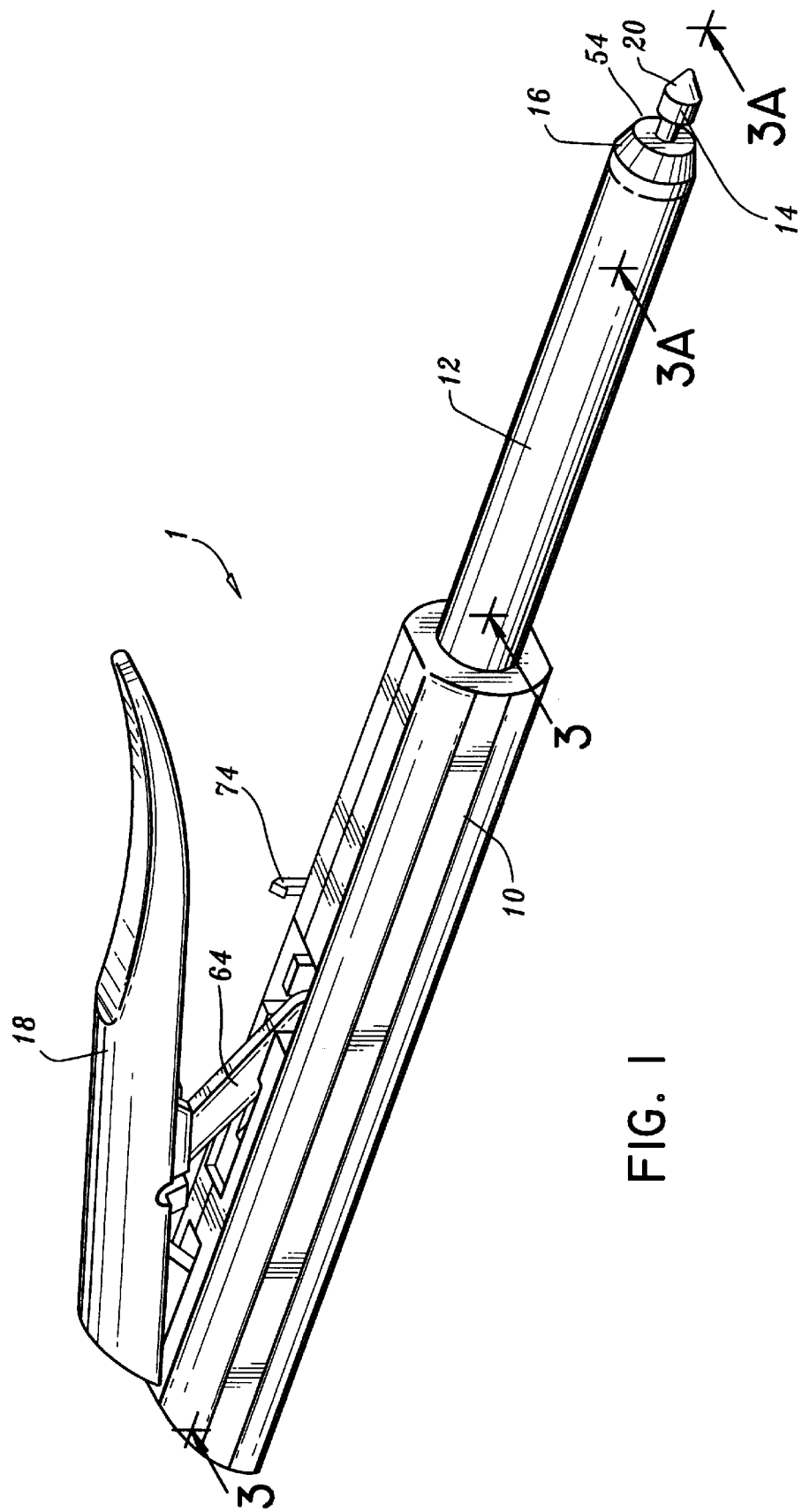
FIG. 1 is a perspective view of surgical apparatus for punching a hole in the vessel.

Referring now to the drawings wherein like reference numerals identify corresponding parts throughout the several views, FIG. 1 illustrates the apparatus 1 of the present disclosure. In brief, apparatus 1 includes a housing 10, an outer tube 12 extending distally from housing 10, an actuator or lever 18 and a penetrating tip 14. Penetrating tip 14, positioned at the distalmost end of the apparatus, is mounted on a rod extending coaxially within outer tube 12 and includes a shielded cutting blade which is exposed to pierce the vessel wall to enable placement of the penetrating tip 14 internally of the vessel. Outer tube 12 has an annular cutter 16 mounted at the distal end which has a circular cutting edge 54. The actuator 18 is mounted to the housing 10 for pivotal movement from an unactuated position (FIG. 1) to an actuated position to advance the outer tube 12 and annular cutter 16 distally toward penetrating tip 14 to form a circular hole in the vessel wall. The annular cutter 16 is advanced after the penetrating tip 14 is inserted through the vessel wall.

Figure 2:
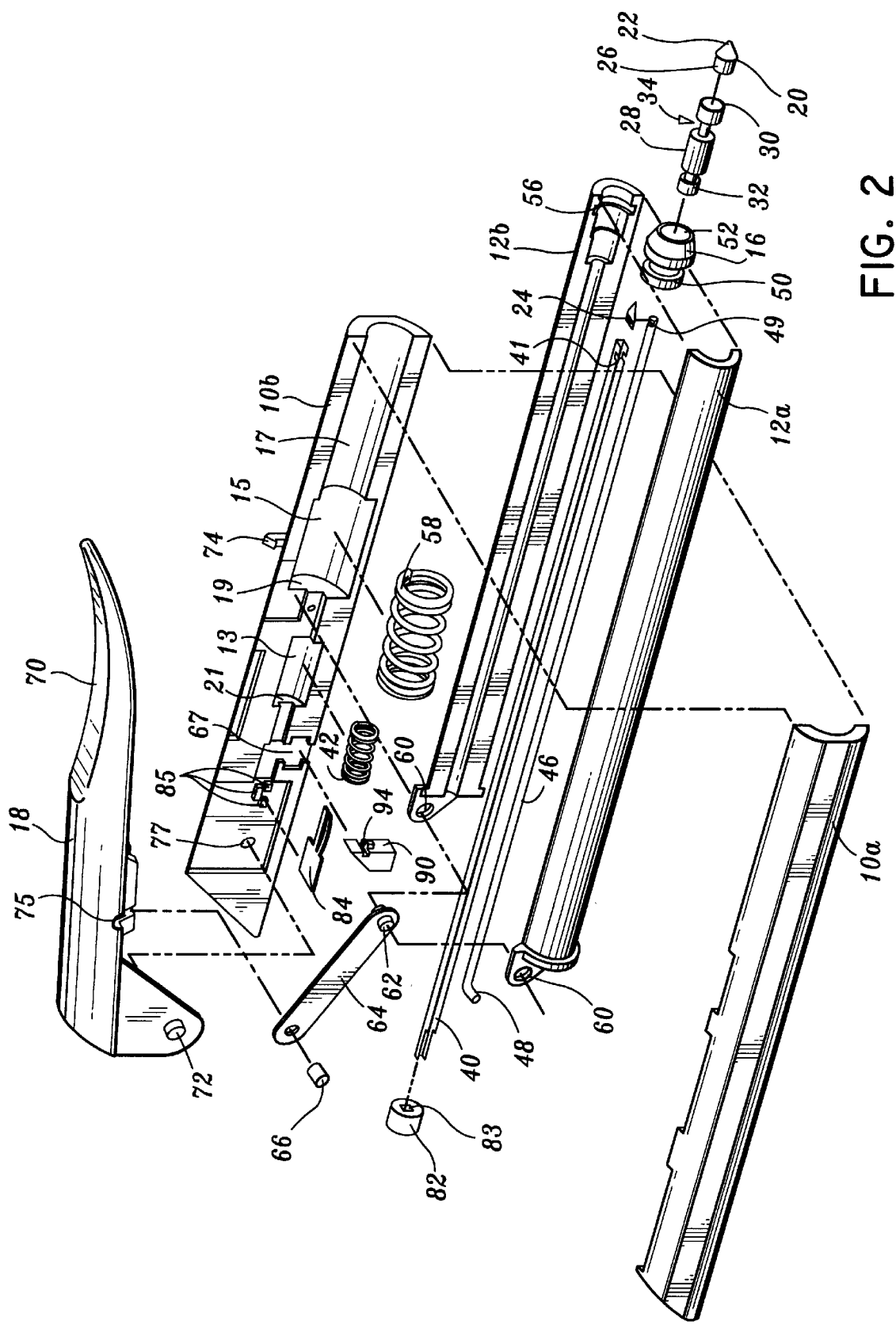
FIG. 2 is an exploded perspective view of the surgical apparatus of FIG. 1.

Turning now to the detailed components of the apparatus, and with initial reference to FIGS. 2, 3A, and 5, penetrating tip includes a shield 20 and a cutting blade 24 which is preferably substantially flat with v-shaped cutting edges 25. Cutting blade 24 is mounted to center rod 46 by engagement of cutout 29 with a notch 49 formed in rod 46. Center rod 46 is fixedly mounted to the housing 10 via leg 48 so the cutting blade 24 remains stationary during use of the apparatus.

Penetrating tip 14 further includes shield 20 having a recess 22 formed in nose 27 and configured and dimensioned to receive cutting blade 24. Shield 20 has a mounting portion 26 which frictionally fits within an opening 30 of punch rod 28. Punch rod 28 includes a proximal fitting 32 which extends through axial opening 52 of annular cutter 16 and is seated in a notch 41 of U-shaped channel 40. Circumferential tissue receiving portion 34 of punch rod 28 cooperates with the annular cutter 16 in the manner described below. U-shaped channel 40 is coaxially and slidably mounted within outer tube 12, extends through axial opening 83 of stop collar 82, and is biased distally by shield spring 42.

Shield spring 42, by biasing channel 40 distally, also biases mounted shield 20 to the distal position. Thus, shield 20 is movable from the initial distal position wherein blade 24 is positioned in recess 22 and thus shielded from tissue to a proximal position wherein spring 42 is compressed and the blade 24 is exposed. FIGS. 3A and 5 illustrate the shield in the distal position to protect the blade and FIGS. 7B, 8 and 9 illustrate the shield in the retracted position to expose the edges 25 of cutting blade 24 to penetrate tissue. As can be appreciated by comparing FIGS. 3 and 7C, when shield 20 is retracted to expose cutting blade 24, shield spring 42 is compressed between stop collar 82 and inner wall 21 of housing 10. Retraction of the shield 20 occurs during initial penetration of the vessel wall which will be discussed in more detail below.

Turning now to the annular cutter 16 and with particular reference to FIGS. 2, 3A and 5, annular cutter 16 includes a cutting edge 54 which is preferably circular in configuration to enable a circular hole to be formed in the vessel. Other shaped cutting edges, however, such as elliptical, are also contemplated. Mounting flange 50 of annular cutter 16 is frictionally engaged within outer tube recess 56 and interacts with lip 12A of outer tube 12 so that movement of outer tube 12 carries annular cutter 16. Tube spring 58 is positioned in recess 15 of housing 10, abuts flange 19 of outer tube 12, and biases the outer tube 12, and thus annular cutter 16, in the proximal direction.

Actuator 18 functions to advance outer tube 12 and cutter 16 towards tissue receiving portion 34 of punch 28. More specifically, outer tube 12 is slid distally by link 64 which is connected at its distal end to outer tube 12 by link pin 62 extending through proximal opening 60. The proximal end of link 64 is connected to actuator 18 via pin 66 extending through aperture 75 formed in actuator 18. Actuator 18 includes at its proximal end a pivot pin 72 which is mounted within aperture 77 of housing 10. Thus, movement of actuator 18 from the open (unactuated) position of FIG. 3 to the actuated position of FIG. 10A moves link 64 to the position shown to slide outer tube 12 distally.

As shown in FIG. 2, outer tube 12 is preferably composed of two halves 12c 12b and housing 10 is preferably composed of two halves 10a, 10b. As noted above, housing halves 10a and 10b together form a recess 15 to receive tube spring 58, a recess 13 to receive shield spring 42 and an elongated recess 17 for reception of outer tube 12. Cavity 67 and tabs 85 are configured for mounting the locking mechanism 80 which will be discussed in detail below. Housing 10 also preferably includes a latch 74 which extends upwardly from the housing toward actuator 18 and is configured to engage a shelf (not shown) in actuator 18 to retain the actuator 18 in the closed position. Thus, latch 74 effectively locks the cutter 16 in the distal position to entrap the tissue between the cutter 16 and the tissue receiving portion 34 of punch 28.

The locking mechanism 80, with initial reference to FIGS. 2 and 3, includes a button 90 and a leaf spring 84 fixedly mounted within tabs 85 formed on housing 10. Leaf spring 84 is bifurcated to form a pair of legs 86 and 88 which bias button 90 downwardly. Button 90 has a recess 94 which is configured to engage a shelf 95 formed in housing 10 adjacent cavity 67 to retain button 90 in the position shown in FIGS. 3. Tabs 92 of button 90 function to limit downward movement of button 90 within cavity 67 when recess 94 is disengaged from shelf 95.

More specifically, the locking mechanism functions as follows. In the initial position of the apparatus 1, legs 86 and 88 of spring 84 engage an edge of the sloped surface 96 of button 90. However, button 90 is retained in the initial position (shown in FIG. 3) by the engagement of shelf 95 and recess 94. When the shield 20 of apparatus 1 is retracted, the proximalmost end of inner channel 40 engages contact surface 97 of button 90 to disengage recess 94 from shelf 95 as shown in FIG. 7. This causes button 90 to slide downwardly in cavity 67 of housing 10 under the downward force of spring leg 88 of leaf spring 84 as shown in FIG. 7A. Continued proximal movement of inner channel 40 as the shield 20 further retracts causes further downward movement of the button 90 until tabs 92, which function as a stop, engage at least one of the walls 93 to limit downward movement of button 90 and retain it within the cavity 67. This position is shown in FIG. 7C. Note the proximal end of channel 40 slides under leg 86 of leaf spring 84.

When shield 20 returns under the force of shield spring 42 to its initial distal position, as shown in FIG. 10, button 90 remains in the downward position under the bias of leg 88 of leaf spring 84. As shown, in this position of shield 20 and inner channel 40, abutment surface 86a of leg 86 abuts the proximalmost end of channel 40, thereby preventing full retraction (proximal movement) of the channel 40 and shield 20.

If the user desires to reuse the instrument to form another hole in the vessel, button 90 can be pressed inwardly (upwardly as viewed in FIG. 10) towards the housing 10 so the edge of sloped surface 96 forces spring leg 86 out of engagement with inner channel 40 and button 90 is returned to its initial position of FIG. 3 with recess 94 engaging shelf 95 of housing 10. Thus, abutment surface 86a of the spring leg 86 is kept out of contact with the inner channel 40 by the edge of sloped surface 96 of button 90 and the shield 20 can once again be retracted.

The operation of the instrument to penetrate and form a hole in the vessel wall will now be described. In the initial position shown in FIGS. 3–5, shield 20 is in its advanced position (biased distally by shield spring 42) to shield blade edges 25 from the tissue. In this initial position, actuator 18 is in the open position such that outer tube 12 which carries annular cutter 16 remains in the proximal position. Spring leg 86 is kept out of the way of inner channel 40 by button 90.

The penetrating tip 14 is pressed against the outer wall of the vessel, causing shield 20 to retract against the force of shield spring 42 as shown in FIGS. 7B and 9 to expose the blade edges 25. The tissue continues to force shield 20 proximally until the penetrating tip 14 has penetrated through the vessel wall into the vessel. At this point, the shield 20 springs back to its distal position by the force of shield spring 42 to shield the edges 25 of blade 24 (See FIG. 8). Note that the retraction of the shield 20 and inner channel 40 forces recess 94 of button 90 out of engagement with shelf 95. This releases spring leg 88 and 86 so that the return of the shield 20 to the distal position causes spring leg 86 to move into the position shown in FIG. 10 to prevent subsequent proximal movement of the inner channel 40 and shield 20.

To form a hole in the vessel wall, actuator 18 is moved from the open (unactuated) position of FIG. 3 to the closed (actuated) position of FIG. 10 to force outer tube 12 and mounted annular cutter 16 to advance towards shield 20. As annular cutter 16 is advanced, cutting edge 54 advances through the tissue around tissue receiving portion 34 of punch 28 to the position shown in FIG. 10A. In this position, tissue is encapsulated between the punch 28 and annular cutter 16. Actuator 18 is retained in the closed position by latch 74 to ensure the tissue remains encapsulated during withdrawal of the instrument. To reuse the apparatus to punch another hole in tissue, button 90 is pressed inwardly to move leg 86 out of the way of inner channel 40 and latch 74 is manually disengaged.

Figure 11:
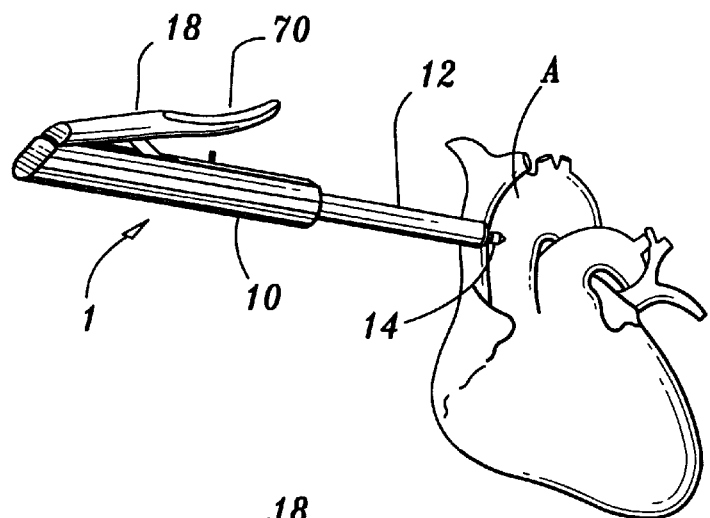
FIGS. 11–13 illustrate the method steps of punching a hole in the vessel wall using the apparatus of FIG. 1.
Figure 12:
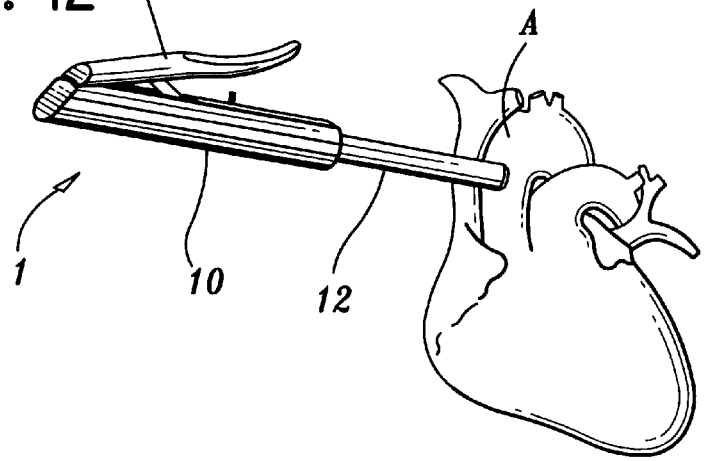
Figure 13:
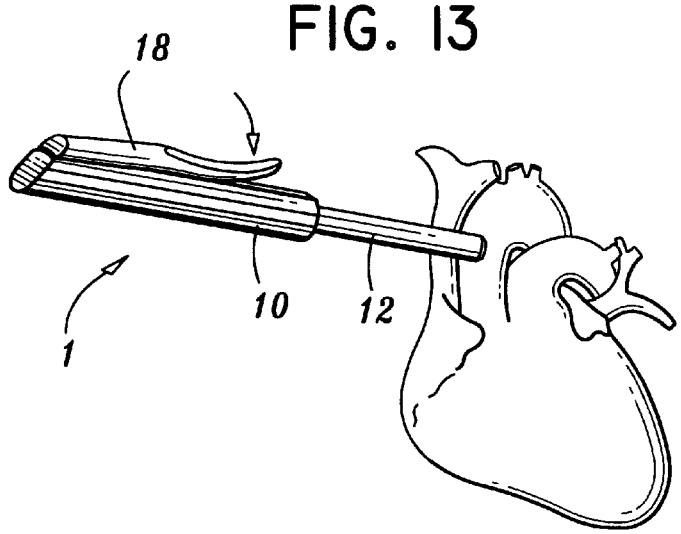
Figure 14:
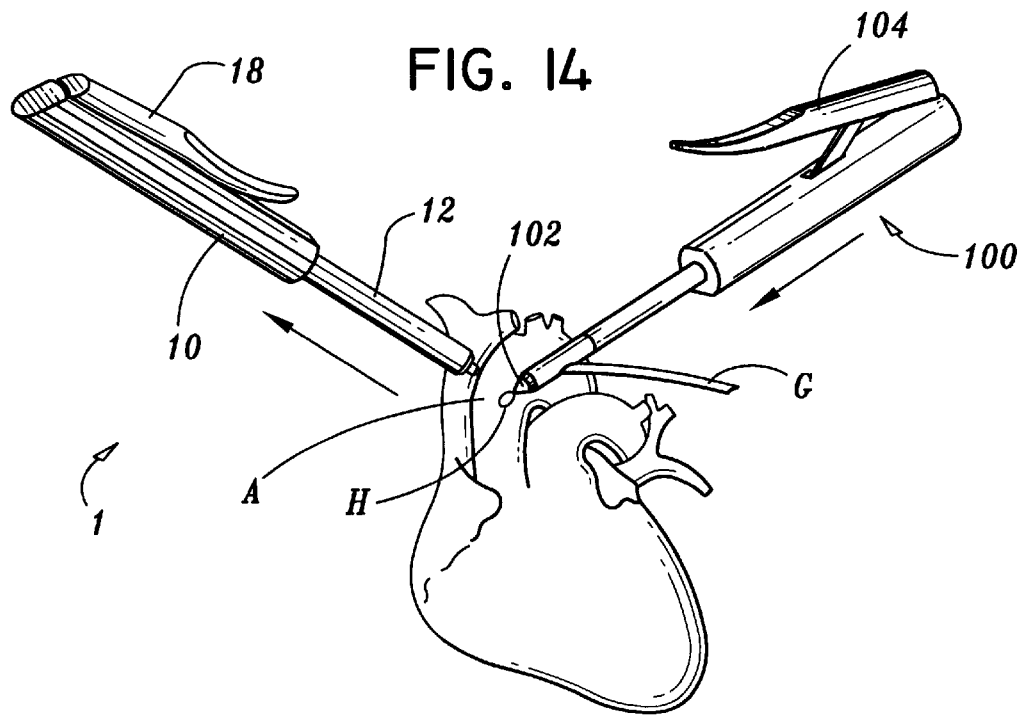
FIGS. 14–15 illustrate one method of attaching a graft to the vessel at the hole formed by the apparatus of FIG. 1.
Figure 15:
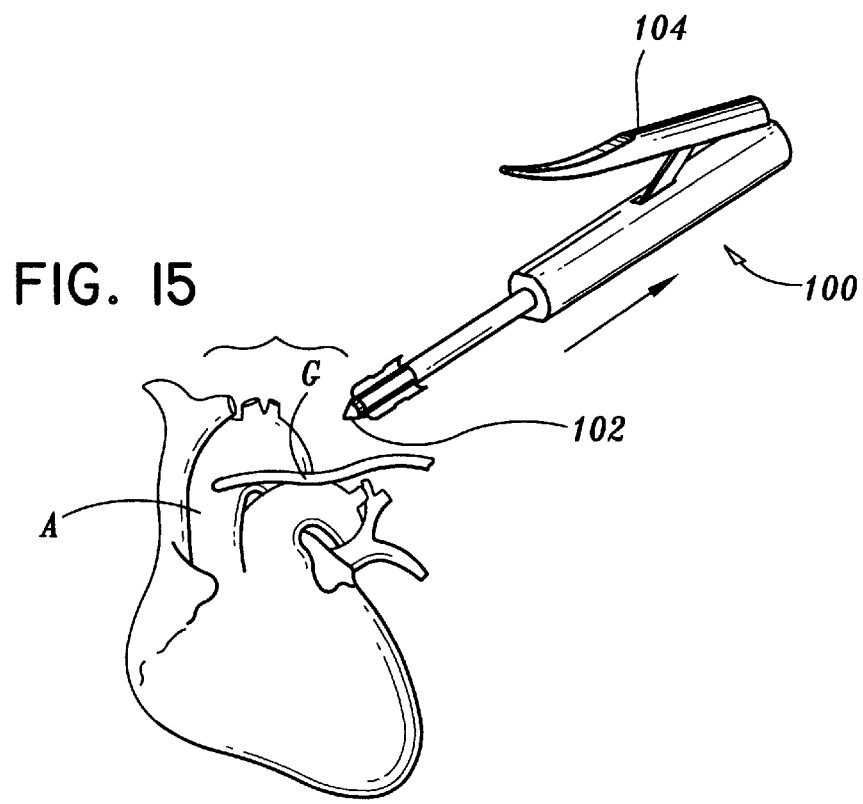

One use of the apparatus will now be described with reference to FIGS. 11–15. This method is described by way of example since the apparatus can be used to punch holes in other vessels and tissue. As shown in FIG. 11, the apparatus 1 is used to form a circular hole in the aorta A as the penetrating tip first pierces the aorta to form an access incision for the instrument (FIGS. 11–12) and the lever 18 is subsequently actuated to advance the outer tube 12 and annular cutter to form a hole in the vessel. The apparatus 1 is then withdrawn, leaving a hole H in the aorta and a graft G is inserted through the hole H by an anastomosis instrument 100. One type of an anastomosis instrument that can be utilized is disclosed in copending application Ser. No. 08/877,701, filed on Jun. 17, 1997 and copending application Ser. No. 08/685,385, filed on Jul. 23, 1996, now U.S. Pat. No. 5,707,380 the contents of which are incorporated herein by reference. This instrument provides an annular array of fasteners upon actuation of the actuator 104 to attach the graft G to vessel A. The apparatus 100 is just one example of how the graft G can be attached and other methods such as suturing are contemplated.

It should be understood that various modifications may be made to the embodiments disclosed herein. For example, the annular cutter could be stationary and the punch can be moved with respect to the cutter. Also, the latch can alternatively be positioned on the button 90 so that the latch would be automatically released when the button 90 is pressed inwardly to reset the instrument for subsequent use. Therefore, the above-description should not be construed as limiting but merely as exemplifications of preferred embodiments. Those skilled in the art will envision other modifications within the scope and spirit of the claims appended hereto.

What is claimed:

1. A surgical apparatus for forming a hole in a blood vessel comprising:

a housing;

an elongated member extending from the housing;

a penetrating tip extending from the elongated member and having a proximal portion and a distal portion, the penetrating tip including a cutting blade at the distal portion to form a first incision in the blood vessel;

the penetrating tip further including a spring biased shield surrounding the cutting blade, the shield and cutting blade being relatively movable in response to penetration of the penetrating tip; and a hole cutter positioned proximally of the penetrating tip, the hole cutter cooperating with the proximal portion of the penetrating tip to form the hole in the blood vessel;

wherein the cutting blade forms the first incision independent of the position of the hole cutter.

2. The apparatus as recited in claim 1, wherein the shield is movable from a first position shielding the blade to a second position exposing the blade.

3. The apparatus as recited in claim 2, further comprising a locking mechanism to prevent subsequent retraction of the shield after the shield has been once retracted and advanced.

4. The apparatus as recited in claim 1, wherein the cutting blade has a cutting edge V-shaped in configuration.

5. The apparatus as recited in claim 1, wherein the hole cutter includes a substantially circular cutting edge to form a substantially circular opening in the vessel.

6. The apparatus as recited in claim 1, further comprising a support for mounting the penetrating tip, the support mounted in an axial bore of the hole cutter.

7. A surgical apparatus for forming a hole in a blood vessel comprising:

a housing;

an elongated member extending from the housing;

a penetrating tip extending from the elongated member, the penetrating tip including a cutting blade;

a hole cutter positioned proximally of the penetrating tip;

wherein the penetrating tip further comprises a shield protecting the cutting blade, the shield being movable from a first position shielding the blade to a second position exposing the blade; and wherein the shield is spring biased distally to the first position, is forced proximally by the vessel wall during penetration of the penetrating tip, and returns to the first position upon penetration of the tip through the vessel wall.

8. The apparatus as recited in claim 7, further comprising an actuator extending from the housing, the actuator actuable to cause relative movement between the hole cutter and the penetrating tip to form a hole in the vessel wall.

9. The apparatus as recited in claim 8, wherein the actuator moves the hole cutter distally towards the shield to sever the vessel.

10. The apparatus as recited in claim 9, further comprising a latch, the latch retaining the actuator in the actuated position to maintain the cutter in a distal position.

11. The apparatus as recited in claim 9, wherein the hole cutter is spring biased proximally.

12. The apparatus as recited in claim 11, wherein the hole cutter is positioned at a distal end portion of the elongated member and the actuator includes a lever connected to the elongated member by a link.

13. A surgical apparatus for forming a hole in a blood vessel comprising:

a housing;

an elongated member extending from the housing;

a penetrating tip extending from the elongated member, the penetrating tip including a cutting blade and a shield protecting the cutting blade, the shield being movable from a first advanced position shielding the blade to a second retracted position exposing the blade;

a locking mechanism to prevent subsequent retraction of the shield after it has been once retracted and advanced; and a hole cutter positioned proximally of the penetrating tip;

wherein the shield is mounted on an elongated rod and the locking mechanism includes a spring movable between a first position to allow retraction of the shield and a second position to prevent retraction of the shield.

14. The apparatus as recited in claim 13, wherein the locking mechanism includes a reset button configured to move the spring from the second position to the first position to allow subsequent retraction of the shield.

15. A surgical apparatus for making a hole in a blood vessel wall comprising a distal portion, means disposed at the distal portion for penetrating the blood vessel wall to provide entry of the distal portion of the apparatus into the blood vessel and means for forming a hole in the blood vessel wall, the penetrating means including a cutting blade and a spring biased shield having an opening for the cutting blade to allow exposure of the cutting blade, wherein the shield and cutting blade are relatively movable to allow exposure of the cutting blade through the opening in the shield, the forming means including a cutter having an axial opening to receive the cut vessel wall portion.

16. A surgical apparatus for making a hole in a blood vessel wall according to claim 15, wherein the shield is movable to expose the cutting blade during penetration of the vessel wall.

17. A surgical apparatus for making a hole in a blood vessel wall comprising a distal portion, means disposed at the distal portion for penetrating the blood vessel wall to provide entry of the distal portion of the apparatus into the blood vessel and means for forming a hole in the blood vessel wall, the penetrating means including a cutting blade and a shield wherein the shield and cutting blade are relatively movable, the forming means including a cutter having an axial opening to receive the cut vessel wall portion, wherein the shield is movable to expose the cutting blade during penetration of the vessel wall, the blade shield being spring biased distally.

18. A surgical apparatus for making a hole in a blood vessel wall according to claim 17, further comprising a locking mechanism configured to prevent subsequent retraction of the shield after the shield has been once retracted and advanced.

19. A method of forming a hole in a blood vessel wall comprising the steps of inserting a cutting member of a penetrating tip of an apparatus directly through the wall to form an access incision for the apparatus as a shield about the cutting member automatically retracts, the shield automatically advancing distally once the penetrating tip has penetrated through the blood vessel wall;

advancing a cutter relative to the penetrating tip to form a hole in the blood vessel wall after the cutting member has formed an access incision.

20. The method of claim 19, further comprising the step of locking the cutter in the advanced position to encapsulate the cut tissue.

* * * * *